(12) United States Patent
Scaife

(10) Patent No.: US 10,773,284 B2
(45) Date of Patent: Sep. 15, 2020

(54) PROCESS AND APPARATUS FOR STERILISING USED HYGIENE PRODUCTS

(71) Applicant: DIAPER RECYCLING TECHNOLOGY PTE. LTD, Singapore (SG)

(72) Inventor: Martin Scaife, Ashford Kent (GB)

( * ) Notice: Subject to any disclaimer, the term of this patent is extended or adjusted under 35 U.S.C. 154(b) by 314 days.

(21) Appl. No.: 15/736,964

(22) PCT Filed: Jun. 17, 2016

(86) PCT No.: PCT/SG2016/050280
§ 371 (c)(1),
(2) Date: Dec. 15, 2017

(87) PCT Pub. No.: WO2016/204697
PCT Pub. Date: Dec. 22, 2016

(65) Prior Publication Data
US 2018/0169721 A1  Jun. 21, 2018

(30) Foreign Application Priority Data

Jun. 17, 2015  (GB) ...................................... 1510642

(51) Int. Cl.
*B09B 3/00* (2006.01)
*B09B 5/00* (2006.01)
(Continued)

(52) U.S. Cl.
CPC .............. *B09B 3/0075* (2013.01); *A61L 2/07* (2013.01); *A61L 11/00* (2013.01); *B09B 3/0083* (2013.01); *B09B 5/00* (2013.01); *A61L 2202/122* (2013.01)

(58) Field of Classification Search
CPC ...... A61L 2/07; A61L 11/00; A61L 2202/122; B09B 3/0075; B09B 3/0083; B09B 5/00; B02C 19/0075
See application file for complete search history.

(56) References Cited

U.S. PATENT DOCUMENTS 5,119,994 A * 6/1992 Placzek ................... A61L 11/00
241/17
6,139,793 A * 10/2000 Vanderwal .............. A61L 11/00
422/1
(Continued)

FOREIGN PATENT DOCUMENTS

DE  G 90 00869.3  5/1990
EP  2 138 244 A1  12/2009
(Continued)

OTHER PUBLICATIONS

International Search Report and Written Opinion of related International Application No. PCT/SG2016/050280, dated Oct. 4, 2016 (13 pages).
(Continued)

*Primary Examiner* — Timothy C Cleveland
(74) *Attorney, Agent, or Firm* — Brinks Gilson & Lione; John C. Freeman

(57) ABSTRACT

The present invention relates to a process and an apparatus for sterilising used hygiene products, comprising the use of an autoclave apparatus. Said autoclave apparatus comprises one or a plurality of rotating internal members. In some embodiments, the plurality of rotating members each concentrically position around a common axis of rotation. In some embodiments, the plurality of rotating members comprises holes of predetermined size, such that the autoclaved products can pass from a central rotating section towards radially outwardly positioned ones. This allows for short processing time with high process performance whilst minimising damage of compounds such as pulp fibre and superabsorbent polymers (SAP) while enabling pure plastic, pulp and SAP streams being separated.

16 Claims, 7 Drawing Sheets

(51) Int. Cl.
*A61L 11/00* (2006.01)
*A61L 2/07* (2006.01)

(56) References Cited

U.S. PATENT DOCUMENTS

| | | |
|---|---|---|
| 2011/0192791 A1 | 8/2011 | Takase et al. |
| 2012/0056021 A1 | 3/2012 | Grimes |
| 2013/0146689 A1 | 6/2013 | Somma et al. |
| 2016/0001296 A1 | 1/2016 | Scaife |

FOREIGN PATENT DOCUMENTS

| | | |
|---|---|---|
| EP | 2596809 A1 | 5/2013 |
| EP | 2596811 A1 | 5/2013 |
| GB | 2 489 254 A | 9/2012 |
| WO | WO 2010/065088 A1 | 6/2010 |
| WO | WO 2014/132128 A2 | 9/2014 |
| WO | WO 2016/049032 A1 | 3/2016 |

OTHER PUBLICATIONS

Supplemental European Search Report from corresponding EP application No. EP16812057.4, 8pages, dated Apr. 16, 2019.

* cited by examiner

PROCESS AND APPARATUS FOR STERILISING USED HYGIENE PRODUCTS

REFERENCE TO EARLIER FILED APPLICATIONS

This application is a 371 national phase of International Application No. PCT/SG2016/050280, filed Jun. 17, 2016, and claims the benefit of the filing date of Great Britain Application No. 1510642.0, filed Jun. 17, 2015, the disclosures of which are incorporated, in their entirety, by this reference.

FIELD OF THE INVENTION

The present invention is a process and related equipment to sterilise products such as used hygiene/sanitary products for recycling purposes. The new sterilisation process has a high process performance whilst also minimising pulp fibre and SAP damage. The process either operates as sterilisation process where raw materials are separated at a later stage in the overall process or, partially or fully separates the pulp and SAP streams whilst the sterilisation process is taking place. The term "hygiene products" and "sanitary products" refers disposable absorbent products, such as baby diapers, adult diapers, incontinence absorbent pads, ladies sanitary pads, absorbent re-fills for durable outer garments, tampons, bed mats, pet diapers and similar disposable articles.

BACKGROUND OF THE INVENTION

Since onset of the autoclave industry, autoclaves have been used to sterilise hygiene waste products. Many of these autoclaves are used in hospital where large amounts of waste are generated and this waste needs to be sterilised prior to deployment into landfill. Medical waste is typically processed in such autoclaves as well as sanitary products. Once infected waste has passed through the autoclave process, this waste can be sent to a standard landfill site or similar. A standard autoclave however is not ideally suited to sterilise waste sanitary products as is described in further detail in the following extract of "Louisiana State University Health Sciences Center-Shreveport, Shreveport, La. USA American Journal of Infection Control (Impact Factor: 2.33).05/2004; 32(3). DOI: 10.1016/j.ajic.2004.04.013:

BACKGROUND: As healthcare institutions search for methods to decrease costs associated with medical waste disposal, many are turning to the use of steam autoclaves. Steam autoclaving theoretically saves money by sterilising large loads of medical waste, making it safe for disposal in a public landfill. There are no national standards for challenging medical waste autoclaves and no guidelines for parameters of sterilisation for medical waste. When Louisiana State University Health Sciences Centre-Shreveport (LSUHSC-S) tested one steam autoclave marketed as a medical waste autoclave, the machine repeatedly failed the tests. A complete description of the challenge testing and results are presented. METHODS: A test scenario was developed using biological indicators (BI) and chemical indicators distributed throughout four loads of clean waste, which were controlled for weight, volume, and density. BI ampules and chemical strips were wrapped inside an adult diaper, which was tied in a common plastic bag and placed inside an open medical waste bag, reflecting common diaper disposal methods. At least five prepared bags were distributed throughout each load. Loads were run at 270° F., 30 pounds per square inch (psi), for 30 minutes, or at 270° F., 30 psi, for 60 minutes.

RESULTS: Bacterial growth occurred in 18 out of 22 ampules, and chemical indicators failed in 19 out of 22 locations. CONCLUSIONS: Steam did not fully penetrate the load, and bacteria were not killed. Despite assurances from marketers of medical waste autoclaves, institutions considering this method must test autoclaves carefully to ensure safety and compliance with local health regulations. Evaluation of a Steam Autoclave for Sterilising Medical Waste at a University Health Center—ResearchGate"

The required penetration of heat to within the product is critical for the process. To resolve this problem, patent applications have been published to address this process constraint such as EP 2 596 809 A1 where the autoclave rotates whilst having either tearing elements attached to the autoclave cylinder and/or tearing elements free-floating within the autoclave cylinder. Once the product has been "torn" heat and "steam" can easily enter the product and product components at which point the sterilisation process begins.

With this process however, four key process considerations must be outlined:

1—Processing closed product reduces process efficiency has heat & steam cannot enter the product. Forming densely packed products within an autoclave and slowly opening these products to start the sterilisation process takes time. Opening up the product as soon as possible reduces the processing time and increases efficiency of the process. Slowly opening the product via a slow tearing reduces process efficiency.

2—Quickly creating air-born fluidized agglomeration of sanitary products or parts of sanitary products allows the hot air to directly penetrate into the sanitary products or parts of sanitary products.

3—Salvaging the raw materials without damaging the materials is key for effective re-sell value, and, as such, grinding the pulp and SAP together within the autoclave is detrimental to raw materials exiting the process. Slowly opening the product within a revolving drum using which includes a significant amount of free-floating heavy parts within the autoclave cylinder also has a detrimental effect to pulp fibre quality.

4—Rotating the entire autoclave assembly adds significant cost to the equipment. Any innovative steps that can reduce the equipment cost and size will help in the global commercialisation of this process that is of significant benefit to the environment.

U.S. Pat. No. 8,177,151 B2 describes a process where salt is added to the autoclave process in order to de-activate the SAP. However, if the SAP can be fully removed from the plastic waste components of the sanitary product, then, this process is no longer required. Adding salt to the process increase environmental impact of the overall recovery process, and, as such, any process enhancements that can remove all SAP from the pulp and plastic streams is also of significant benefit to the environment.

SUMMARY OF THE INVENTION

In a first aspect, the present invention is an autoclave process for sterilising hygiene products, comprising the steps of a. providing autoclave equipment, operating as either a continuous process or batch process and comprising one or more rotatably mounted internal bodies;
b. rotating the one or more internal bodies, preferably at a speed of more than 1 RPM, preferably around an axis that is inclined relative to the horizontal.

The rotating of the internal body or bodies may apply between 0 to 1 G of acceleration forces to products so as to cause avalanching of the products within the rotating body or bodies. The process may further comprise the step of positioning product-shredding devices within a rotating body of the autoclave, preferably at predetermined positions within the path of avalanching products, such that products within the rotating body are interacting with the product-shredding devices such that they are pulled apart, wherein the product shredding devices preferably comprise multiple finger and preferably do not exhibit sharp edges. The process may further comprise the step of separating parts of the products into more than one processing sections separated by further rotating members within the autoclave, wherein the further members are preferably rotating around a common rotating axis, and optionally at differing speeds or directions. The products may enter a central rotating processing section and may be separated into parts migrating from the central processing section radially outwardly through holes in the rotating member into sections of the further rotating members positioned radially further outwardly. Plugging of the holes in the rotating processing section(s) may be prevented by positioning the leading edge of the holes in the direction of rotation at a process point where the products being processed within the autoclave are essentially dry.

Optionally, pulp fibres of parts of the products may be opened up by opening devices.

In a second aspect, the present invention relates to operating multiple such autoclave processes, which may be connected in parallel or series, and each of which may be operated as a continuous process or batch process. Each of the multiple processes may be operated with at least one variation of the process settings for the respective autoclave equipment, the process settings being selected from the group consisting of
  (i) pressure settings;
  (ii) temperature settings;
  (iii) moisture settings;
  (iv) process dwell time settings.

In this operation, parts of the processed products may be separated by size by segregating by passing smaller parts through a first plurality of holes of the rotating body of a first autoclave process and feeding the segregated portions of the parts of the products to different subsequent autoclave processes. Optionally, the rotating body of the first autoclave process comprises holes of different size in different regions, through which differently sized parts of the products are passing and wherein the differently size parts are fed to different further autoclave process(es) of the multiple autoclave processes. Preferably the autoclave process or the multiple autoclave processes may be operated alone, jointly, or with other process modules preferably selected from the group consisting of balers, pelletizers, and material in-feed stations, upon fitting to support bodies sized to conform to ISO shipping container standards.

In a further aspect, the present invention relates to an apparatus for sterilising used or waste hygiene products comprising an autoclave, wherein the autoclave is adapted to be operated in a continuous process or batch process mode, wherein the autoclave comprises one or more rotating internal bodies, preferably around a horizontally inclined axis, and preferably adapted to apply between 0 to 1 G of acceleration forces to the products. Preferably, any or all of these rotating bodies are adapted to rotate and at least the speed of an innermost rotating body is set to cause avalanching products therein. Optionally, the rotating bodies comprise(s) one or more devices selected from the group consisting of
  internal transport devices, preferably paddles, designed to transport product axially within the rotating body;
  product-shredding devices,
    positioned so as to allow interaction with avalanching product or product parts, preferably rotatably mounted, preferably at a speed of more than 1 RPM,
    and preferably comprising multiple fingers, and preferably designed without sharp edges so as to allow pulling apart rather than cutting of the products or parts thereof;
  opening devices to allow opening up of pulp fibres, if present in the products.

The autoclave may have more than one processing sections separated by one or more rotating body or bodies, adapted to allow products or parts thereof to pass from one section to a neighbouring one, preferably through holes of predetermined size. Optionally, processing sections are essentially concentrically positioned around a common axis of rotation, further preferably adapted to allow the products or parts thereof to pass from a central rotating section towards radially outwardly positioned ones. A rotating body may comprise a first plurality of holes and a second plurality of holes differing in size or shape, to allow segregation and separation of parts of products.

The present invention also relates to multiple autoclave apparatus connected in parallel or series, wherein the autoclaves are adapted to operate with varying process settings, the process settings being selected from the group of
  (i) pressure settings;
  (ii) temperature settings;
  (iii) moisture settings;
  (iv) process dwell time settings.

In yet a further aspect, the present invention relates to an equipment for sterilising used or waste hygiene products comprising an autoclave apparatus or multiple autoclave apparatus, further optionally comprising additional modules that are preferably selected from the group consisting of balers, pelletizers, and material in-feed stations, wherein the equipment is housed within a support body that conforms to ISO shipping container standards, and which is optionally adapted to be plugged together with similar equipment.

BRIEF DESCRIPTION OF DRAWINGS

FIG. (1) outlines a cross section of an autoclave according to the present invention, showing an autoclave pressure-vessel (1A) within which a sterilising environment of elevated temperature, and/or elevate pressure can be achieved. The pressure-vessel comprises an entry area (1B) at the beginning of the process path where products enter the autoclave process, and further a rotary destruction device (1C). The products being processed within the autoclave (1D) are shown in the lower portion of the pressure vessel. It should be noted that within the present context, the terms "lower"/"upper" are to be understood as being oriented along gravity.

FIG. (2) outlines a cross section of a further execution of an autoclave according to the present invention, showing a rotating body (2A) within the autoclave with an entry area (2B) at the beginning of the process path where products enter the autoclave equipment and a rotary destruction device (2C). The products being processed within the autoclave (2D) are shown in the lower portion of the rotating body (2A). (The autoclave further comprises an outer pressure housing (2E), within which an environment of elevated temperature and/or elevated pressure can be achieved.

Figure 3:
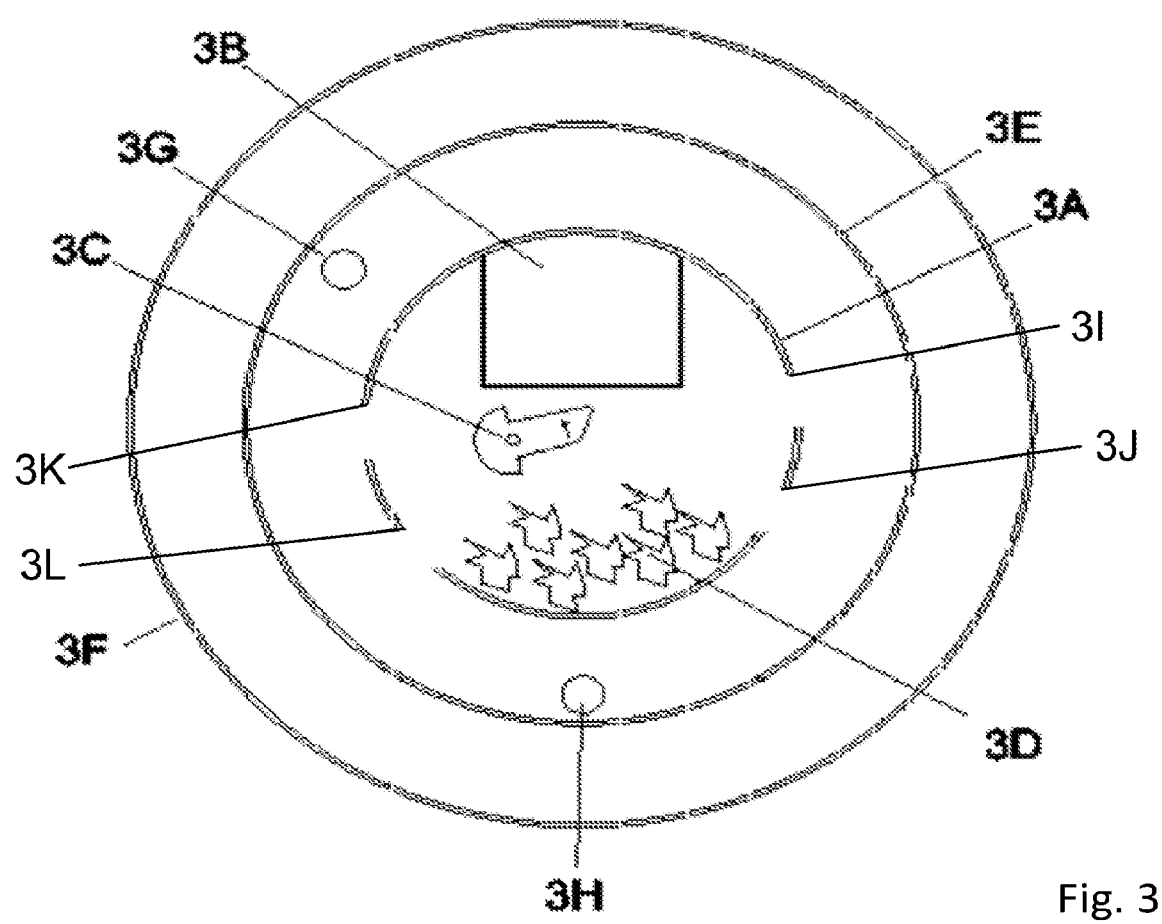

FIG. (3) outlines a cross section of a further execution of an autoclave according to the present invention, showing a rotating body (3A) within the autoclave with an entry area (3B) at the beginning of the process path where products enter the autoclave equipment and a rotary destruction device (3C). The products being processed within the autoclave (3D) are indicated in the lower portion of the rotating body (3A). This execution further comprises a secondary rotating body (3E) within the autoclave. The rotating body (3A) may include a plurality of holes (e.g., holes 3I, 3J, 3K, and 3L). It will be appreciated that the holes shown in FIG. 3 are schematic in nature and are not to be used to denote a particular shape, size, number, position, or distribution of the holes. The autoclave further comprises an outer pressure housing vessel (3F) to enable achieving an environment of elevated temperature, and/or elevated pressure. Further shown are opening devices (3G, 3H) designed to open-up closed pulp fibres.

Figure 4:
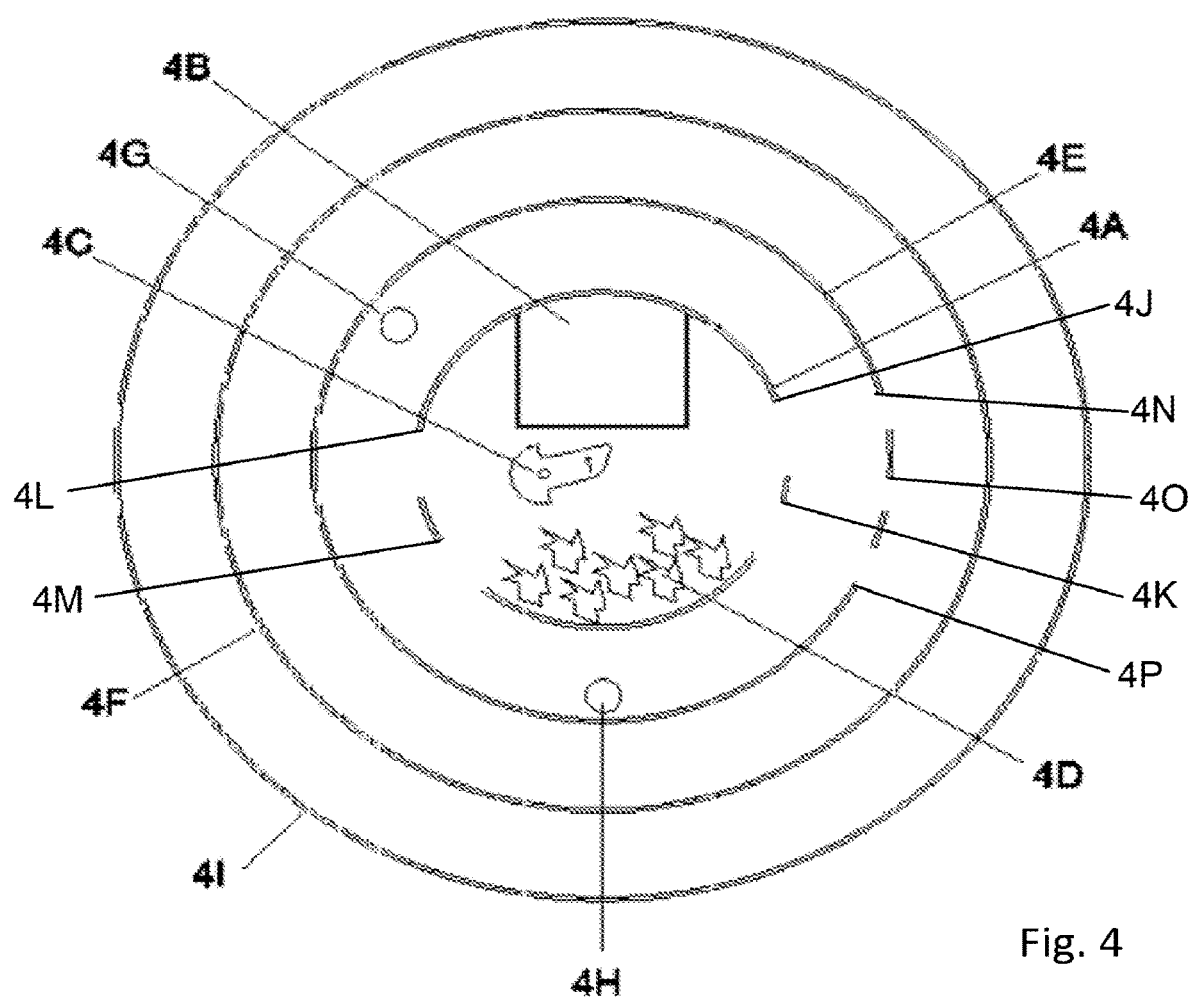

FIG. (4) outlines a cross section of yet a further execution of an autoclave according to the present invention, showing a rotating body (4A) within the autoclave and an entry area (4B) at the beginning of the process path where products enter the autoclave equipment and a rotary destruction device (4C). The products being processed within the autoclave (4D) are indicated in the lower portion of the rotating body (4A). In this execution, the autoclave comprises a secondary rotating body (4E) and a further rotating body (4F). The rotating body (4A) may include a plurality of holes (e.g., holes 4J, 4K, 4L, and 4M). The secondary rotating body (4E) may also have a plurality of holes (e.g., holes 4N, 4O, and 4P). The holes on the secondary rotating body (4E) may be smaller than the holes on the rotating body (4A). It will be appreciated that the holes shown in FIG. 4 are schematic in nature and are not to be used to denote a particular shape, size, number, position, or distribution of the holes. Further opening devices (4G, 4H) are designed to open-up closed pulp fibres. The autoclave further comprises an outer pressure housing vessel (4I) of the autoclave within which an environment of elevated temperature, and or elevate pressure can be achieved.

FIG. (5) outlines a cross section of a further execution of an autoclave according to the present invention, showing the autoclave pressure-vessel (5A) within which an environment of elevated temperature and/or elevate pressure can be achieved. Through an entry area (5B) at the beginning of the process path the products enter the autoclave equipment. Further shown within the pressure vessel (5A) is a rotary destruction device (5C) and products (5D) as being processed within the lower portion the autoclave.

FIG. (6) outlines a cross section of a similar execution of an autoclave according to the present invention, showing an autoclave pressure-vessel (6A) within which an environment of elevated temperature and or /elevate pressure can be achieved with an entry area (6B) at the beginning of the process path where products enter the autoclave equipment. In this execution, the autoclave comprises a first (6C) and a second (6D) rotary destruction device. The products being processed within the autoclave (6D) are indicated within the lower portion of the pressure vessel.

FIG. (7) outlines a cross section of a further execution of an autoclave according to the present invention, showing an autoclave pressure-vessel (7A) within which an environment of elevated temperature and/or elevate pressure can be achieved with an entry area (7B) at the beginning of the process path where products enter the autoclave equipment. The autoclave comprises a first rotary destruction device (7C) and a differently shaped second rotary destruction device (7D) with multiple fingers 7F (e.g., three fingers 7F which do not have sharp edges, as shown). Products (7E) being processed within the autoclave are indicated within the lower portion of the autoclave.

FIG. (8) outlines a cross section of yet a further execution of an autoclave according to the present invention enclosed within a common modular housing such as a shipping container housing, wherein the outer module (8A) may interface with other process items. The autoclave further comprises a pressure vessel (8B).

Figure 10:
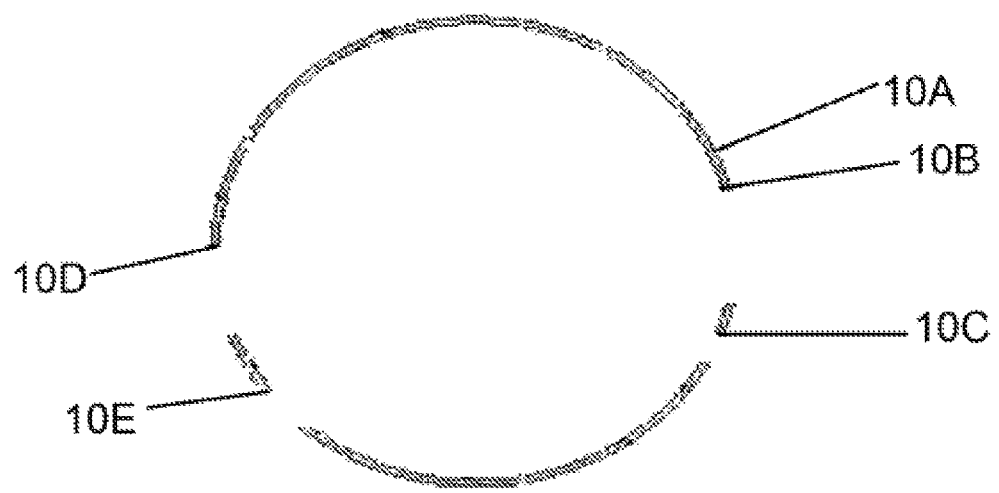

FIG. (9) outlines a cross section of a further execution of an autoclave according to the present invention, showing a common modular housing such as a shipping container housing, comprising an outer module (9A) which interfaces with other process items and a pressure vessel (9B) of the autoclave. FIG. (10) outlines a cross section of a further execution of an autoclave according to the present invention, showing a rotating body (10A). The rotating body (10A) may include a plurality of holes (e.g., holes 10B, 10C, 10D, and 10E) with different sizes/shapes in different regions. For example, as shown, the hole 10B may be larger than the hole 10D, the hole 10D may be larger than the hole 10E, and the hole 10E may be larger than the hole 10C. It will be appreciated that the holes shown in FIG. 10 are schematic in nature and are not to be used to denote a particular shape, size, number, position, or distribution of the holes.

DETAILED DESCRIPTION OF THE PRESENT INVENTION

For explanatory purposes, the equipment and the process according to the present invention are described by referring to particular features as explained in the respective figures. This should, however, not seen in a limiting way, and individual features or elements can be used as such and on their own or in combination with any other feature.

Within the actual autoclave process according to the present invention, a drum is revolving within which hygiene products are contained. Without intending any limitation, hygiene products may be used or waste baby or adult incontinence articles, feminine hygiene articles and the like. Such products typically comprise plastic web materials such as film or nonwovens, which envelop absorbent materials, often cellulosic pulp fibres and often in combination with superabsorbent polymer (SAP) materials. The products may be loaded with any bodily exudates, typically human exudates such as urine, faeces, blood, menses and the like, which require sterilisation before any further treatment.

The present invention relates to an equipment of an autoclave and to a process for operating such an equipment. The equipment can comprise one or more autoclaves that may be arranged and operated either a continuous process or batch process. The autoclave comprises at least one internal body that is adapted to rotate or be operated rotatingly. The rotating internal body may apply between 0 to 1 G of acceleration forces to products being transported within the rotating body. The rotating body may be rotated at a speed to cause avalanching products within the rotating body. The rotating body may comprise internal transport devices, preferably paddles, designed to transport product within the rotating body when g-forces of under 1 G of acceleration forces are applied to the products being transported within the rotating body. Products within the equipment may be hit and further shredded by product-shredding devices housed within the autoclave. A rotatory shredding device and/or devices may be rotating at a speed higher than 1 revolution per minute. Optionally, the shredding device has no sharp surfaces. A rotatory shredding device and/or devices may comprise multiple fingers placed in a configuration to pull-apart products being processed within the autoclave. A product destruction device and/or devices may be positioned at predetermined locations to receive products and/or segregated products that are avalanching at predetermined locations within the autoclave process. The autoclave may comprise more than one processing chamber or section. Product may enter a central rotating chamber wherein parts of the products being processed can migrate into outer chambers, optionally through holes comprised in the rotating chamber(s). The holes in the rotating chamber(s) may be positioned such that they start at a process point where the products being processed within the autoclave are dry and as such, and hole plugging cannot occur or at least reduced. Parts of the products being processed can pass into outer chambers where-in the outer chambers have rotating devices to open up pulp fibres.

The present invention also relates to a process being operated on and an equipment comprising multiple autoclaves that may be connected or arranged in parallel or series. The autoclaves are preferably adapted to be and preferably are operated with varying process settings, said process settings being selected from the group of
 (i) pressure settings;
 (ii) temperature settings;
 (iii) moisture settings;
 (iv) process dwell time settings.

A rotating body may be rotated at a speed to cause avalanching products wherein the axis of the rotating body is not horizontal. The rotating body may comprise a plurality of holes to allow components of products within the rotating body to exit wherein the rotating body has holes located down-stream of the rotating body wherein these holes have a larger diameter. The at least one autoclave may suitably be housed within a support body that conforms to ISO shipping container standards. Optionally, multiple bodies and/or modules and/or shipping containers can be plugged together to increase throughput capacity. The support body may interface directly with other process modules such as balers, pelletizers, material in-feed stations.

The present invention relates to an apparatus for sterilising used/waste hygiene products with an autoclave and to a process for operating such an equipment. The equipment can comprise one or more autoclaves that may be arranged and operated either a continuous process or batch process. The autoclave comprises at least one internal body that is adapted to rotate or be operated rotatingly. Thus the rotating body can apply between 0 to 1 G of acceleration forces to products being transported within the rotating body. The rotating body may be adapted to rotate at a speed to cause avalanching products within the rotating body. The rotating body may comprise internal transport devices, preferably paddles, designed to transport product within the rotating body when g-forces of under 1 G of acceleration forces are applied to the products being transported within the rotating body. Optionally, products within the rotating body hit specifically designed product-shredding devices housed within the autoclave. The autoclave may comprise a rotatory shredding device and/or devices is/are rotating at a speed higher than 1 revolution per minute. The rotatory shredding device may be designed to have no sharp surfaces. The rotatory shredding and/or devices may comprise multiple fingers placed in a configuration to pull-apart products being processed within the autoclave. The autoclave may comprise at least one product destruction device positioned at predetermined location(s) to receive products and/or segregated products that are avalanching at predetermined locations within the autoclave process. The autoclave may comprise more than one processing chamber. The autoclave may comprise a central rotating chamber wherein parts of the products being processed can enter and migrate into outer chambers. The rotating chamber may comprise through holes through which products being processed can migrate into outer chambers. The holes in the rotating chamber(s) may be positioned at a process point where the products being processed within the autoclave are dry and as such, hole plugging is reduced or avoided. Optionally, wherein products being processed can migrate into outer chambers through holes in the rotating chamber where-in the outer chambers have rotating devices to open up pulp fibres.

Optionally, the axis of the rotating body is not horizontal. The rotating body may have a plurality of holes to allow components of products within the rotating body to exit wherein the rotating body has holes located down-stream of the rotating body wherein these holes have a larger diameter.

The autoclave may be housed within a support body that conforms to ISO shipping container standards and multiple bodies and/or modules and/or shipping containers can be plugged together to increase throughput capacity and may interface directly with other process modules such as balers, pelletizers, material in-feed stations.

The invention includes process and apparatus and methods for treating and sterilising used hygienic product waste including, drying, and to some extent can also pre-separate and/or fully separates components enclosed with the absorbent sanitary products allowing full or partial recovery of the raw materials used within the hygienic product such as SAP, pulp, and a variety of plastic components. By using an autoclave with integrated shredding device and internal rotating devices that move fast enough allow the product being processed "air-born" within the autoclave and speed up the sterilisation process. Further embodiments outlined herein are for drying the waste and separating the waste, and creating segregated process areas within the autoclave or multiple autoclaves where dedicated environments can be maintained to aid sterilisation and dry the materials that are best suited to the materials at that particular point in the process. Further embodiments outlined herein are to incorporate the technology into a plug & play modular format, which also included standard ISO shipping container format(s). For avoidance of any doubts, it should be noted the term "apparatus" stands both for the plural and the singular form thereof.

Figure 1:
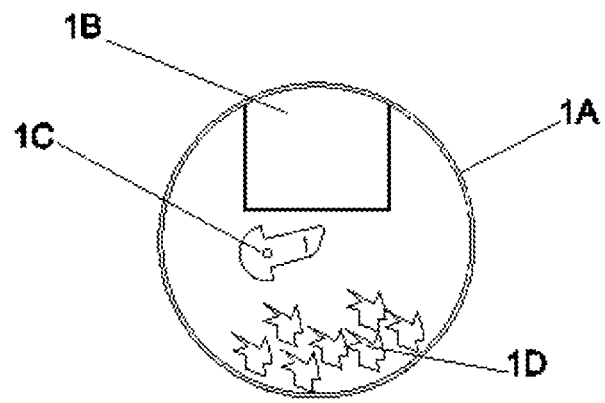

The general concept of the present invention is shown in FIG. 1, where the hygiene products, are entering the system enter via inlet chute (1B). A rotating body or drum (1A) rotates at a predetermined RPM (rotation per minute). The product enclosed within the drum (1D) is transported by the drum for processing within the drum (1A). If a drum with a given diameter rotates slowly, say at less than 10 RPM or even less than 1 RPM, the product rolls around on the floor of the drum. If the drum rotates quickly, say at 1000 RPM, the centrifugal forces within the drum are over 1 G (gravity), and as such, product remains stuck to the surface of the drum. If the drum rotates at an intermediate speed so as to create centrifugal forces of less than 1 G, e.g. 0.9 G, the products of the lowermost portion of the drum remain attached to the wall for a fraction of the rotation but will be falling off the inner drum surface before a 12 O-Clock position (i.e. the uppermost position against the direction of gravity) is reached. This is also referred to herein as the "avalanche speed", at which, the avalanche of products can be used to (1) make products within the drum air-borne, and (2) to feed products into a variety of processes positioned in the path of the avalanching materials. A skilled person will readily realize that this effect is depending on the diameter of the drum, and that the rotational speed (in RPM) needs to be adapted thereto.

The, the autoclave may comprise a rotary destruction device, in FIG. 1, show as a rotary shredding device or shredder 1C that is rotating at e.g. 2500 RPM in a clockwise direction, i.e. in the opposite direction as the drum is rotating, though it can also rotate at between 1-100 000 RPM in any direction. As products hit 1C, they often break apart, primarily due to the force of the impact. Within the autoclave this process and arrangement has significant advantages in that (i) products being air-borne, such that the hot sterile air quickly penetrates the products; (ii) the rotary shredding device is very effective to open up the products; and (iii) the positioning of the rotary shredding device provides very suitable locations to inject the steam into the process.

Figure 2:
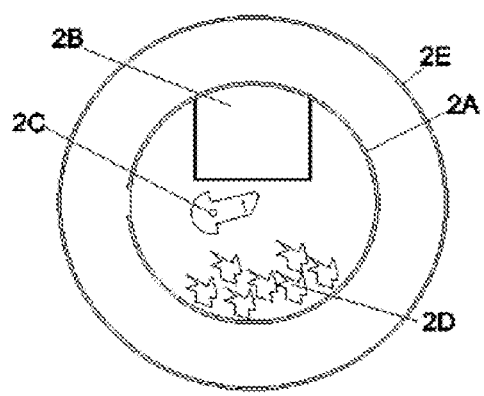

Optionally, the shredding device may comprise internal transport devices, preferably paddles, such that, when g-forces of less than 1 G of acceleration force are applied to the products, said products are transported axially within the rotating body. In order to demonstrate the separating of the function of the rotating body as may be executed as a rotating drum and of the pressurized vessel, FIG. 2 shows a system wherein the actual pressure vessel (2E) does not need to rotate, thus this also opens up new opportunities for the rotating drum (2A) inside the pressure vessel to be modified, such as adding perforated holes and similar.

The size of the system may be adapted according to the size and type of the products to be treated. The diameter of a rotating device may range from about 50 cm to well over 2 m and the length of such a drum may range from 50 cm to well over 5 m and even more. Optionally, the rotating axis of the rotating device may be inclined versus the horizontal, such that the products may also be transported axially from the entry to the exit.

Such a design also has some cost benefit implications in the manufacturing costs of the system and if designed correctly, does open up design options for operators to gain better access to the autoclave. An alternative execution of this design is shown in FIG. 3, where the internal rotating drum (3A) is porous or apertured and finer particles can migrate through the pores, holes, or apertures into a radially outwardly positioned second drum section (3E). This not only "aerates" the materials to be processed by further creating enhanced sterilisation efficiency, it allows also further processing to be adapted to the processing of those particular component specification and sizes. In the instance of hygiene products, the drum (3A) could be perforated with holes of 10 mm, but these could range between 0.1-1000 mm, that allows pulp and SAP fibres to migrate outside of the drum (3A). Once landing on drum surface of the second drum section (3E) that is also rotating, these fibres are transported to opening devices, here shown as a rotating opening rolls (3G, 3H) that open any close clumps of fibres. The opening devices (3G, 3H) can be continuous throughout the entire axial length of the second drum (3E) but can also be non-continuous and be positioned only in specific locations of the drum. If the second drum (3E) was for instance rotating anti-clockwise with a rotational velocity to create 0.9 G, but this could be between 0 and 1 G, airborne pulp fibres would hit an opening device (3G) that would open up fibres further for maximum sterilisation efficiency. Furthermore, the exact rotation speed of (3E) could be adjusted so as to allow pulp fibres to hit and be processed by (3G). Furthermore, the positions of the rotating devices (3G, 3H) are suitable locations to inject steam into the process.

A further execution this design is in FIG. 4, where the rotational speed of the internal rotating drum (4A) is set to create the preferred avalanching condition. The internal rotating drum is apertured or porous such that finer particles can migrate there through into the section of the second drum (4E), which is also is porous or apertured through which finer particles can migrate into the section of a third drum (4F). The second porous drum (4E) could be perforated with holes smaller than the internal rotating drum (4A), e.g. of 2 mm, but these could range between 0.1-1000 mm, so as to allow for example SAP to migrate out from the section of the second drum (4E) to be collected in the section of the third drum (4F). By rotating (4F) for instance anti-clockwise with a rotational velocity to create centrifugal forces of about 0.96 G, but this could be between 0 and 1 G, airborne SAP would have maximum air exposure, as they would be leaving the drum for a considerable time frame and being fully air-born.

The choice for materials for the internal components of the autoclave is not particularly limiting, as long as it could satisfy the mechanical and sterilisation requirements, and thus could be made—without intending any limitation—from mild steel, coater steal, stainless steel, aluminum, silicon, vulcanized silicon, ceramic to name but a few.

Figure 5:
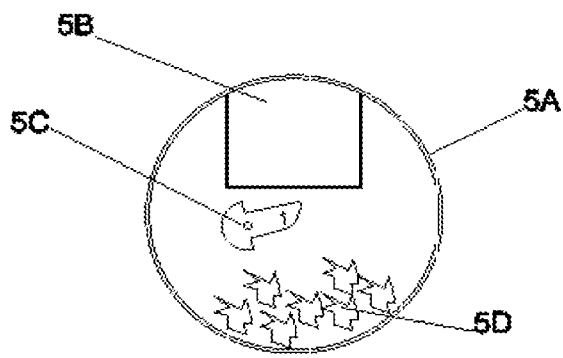

The opening device shown in FIG. 1) as (1C), would however not be the most efficient method to open the hygiene products. Referring to FIG. 5, a preferred process execution is described, wherein products are entering the system through the entry area or opening (5B). The composition of the entering products are often un-known, and small products, large products, even large bags of products may enter the process. Thus, the entry area (5B) is a simply designed system that has no "pinch" points with other parts of the machine. Also, to note, the entry area (5B) may comprise sharp edges, but preferably may be a blunt device so as to minimize the cutting effect to the hygiene products as any cutting process creates the risk of creating small plastic components that stand that risk contaminating the pulp stream through later sieving processes.

Figure 6:
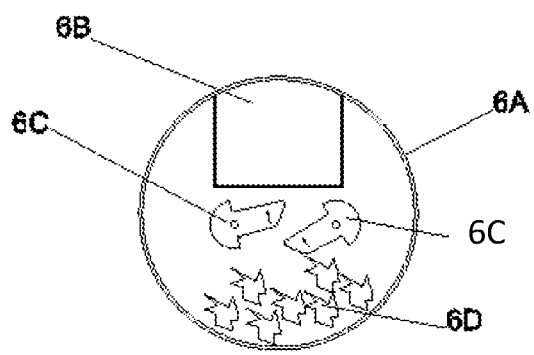

As the process progresses, the shape and state of the shredded components of the hygiene products are becoming more similar, and as such, more efficient shredding devices can be used. FIG. 6 shows a dual rotating shredding device (6C) that can potentially hit the components of the hygiene products more effectively.

Figure 7:
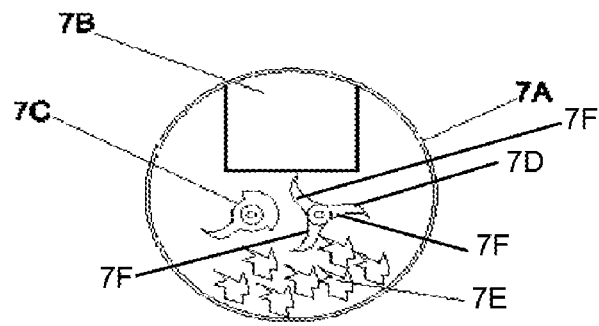

FIG. 7 shows a dual rotating shredding device (7C, 7D) that can rotate at a slower speed and slowly tears the hygiene components apart.

Figure 8:
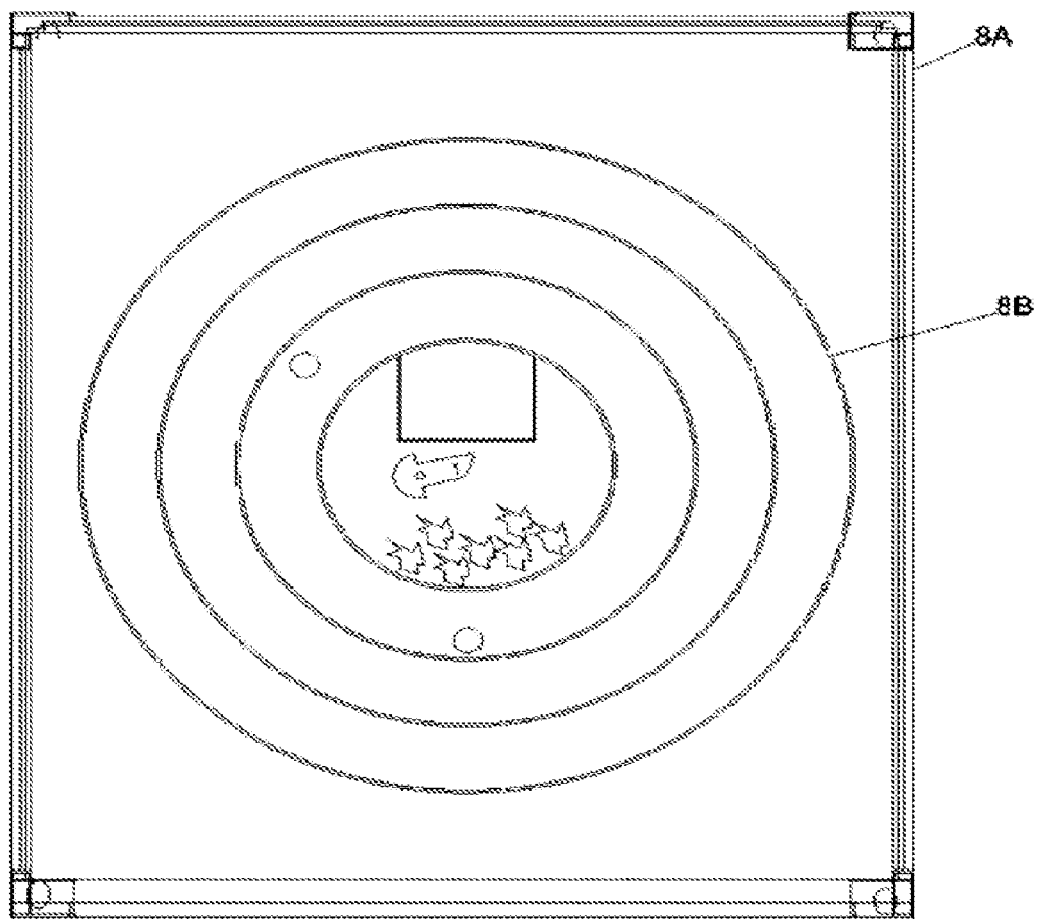

The present invention provides significant benefits: Reducing start-up costs as well as allowing to have a portable system, as well as having an expandable system, as well as having a low cost system that can be placed in close vicinity to areas generating waste, significantly improve viability of the technology. FIG. 8 shows a concept where this new apparatus and process is housed within a standardized shipping container. This means no dedicated installation is required; the equipment can be simply unloaded and started. It also allows for multiple systems to be plugged together increasing through put capacity. This capacity could be added in parallel or series, and, if the systems are plugged together in series, each system could be set-up to optimal mid-range settings for that particular process. For instance, considering in a set up as shown in FIG. 4, the section of the third drum (4F), may separate out SAP that could be processed in a further dedicated sterilisation process (final sterilisation) where, for example, the temperatures in this process could be slightly higher than the initial process and slightly drier to aid drying of SAP.

Figure 9:
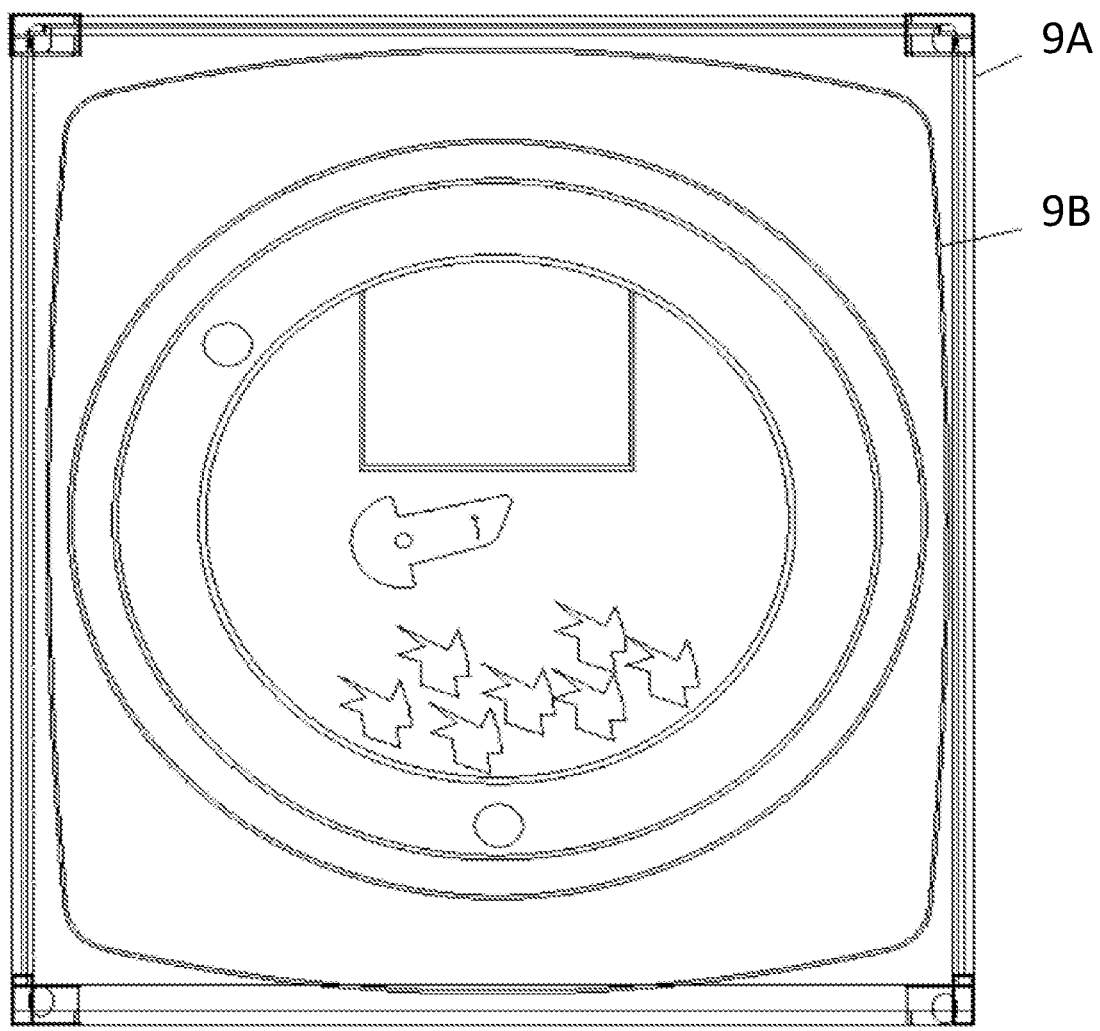

FIG. 9 shows an enhancement to this concept where the outer walls of the pressurized container have been specifically modified to allow better integration into shipping container format and better operator access around the autoclave components.

The invention claimed is:

1. An autoclave process for sterilizing a product, comprising:
  providing an autoclave equipment, operating as either a continuous process or a batch process, said autoclave equipment comprising an outer pressure housing vessel and a rotatably mounted internal body that supports a product thereon;
  rotating said rotatably mounted internal body around an axis that is inclined relative to a horizontal plane;
  separating parts of said product into a plurality of processing sections defined by a second rotatably mounted internal body and a third rotatably mounted internal body within said autoclave equipment, wherein said rotatably mounted internal body, said second rotatably mounted internal body, and said third rotatably mounted internal body rotate around a common rotating axis, wherein said product enters into a central rotating processing section defined in part by said rotatably mounted internal body and is separated into parts migrating from said central rotating processing section radially outwardly through holes in said rotatably mounted internal body into one of said plurality of processing sections, and wherein said second rotatably mounted internal body and said third rotatably mounted internal body are positioned radially further outwardly with respect to said rotatably mounted internal body.

2. The autoclave process according to claim 1, wherein said rotating said rotatably mounted internal body applies between 0 to 1 G of acceleration forces to said product so as to cause avalanching of said product within said rotatably mounted internal body.

3. The autoclave process according to claim 1, further comprising positioning a product-shredding device within said rotatably mounted internal body of said autoclave equipment such that said product within said rotatably mounted internal body interacts with said product-shredding device such that said product is pulled apart, wherein said product shredding device comprises multiple fingers that do not exhibit sharp edges.

4. The autoclave process according to claim 1, further comprising opening up pulp fibres of parts of said product being processed by opening devices positioned in one of said plurality of processing sections.

5. An autoclave process, comprising:
  performing a first autoclave process comprising:
    providing a first autoclave equipment, operating as either a continuous process or a batch process, said first autoclave equipment comprising a first outer pressure housing vessel and a first rotatably mounted internal body that supports a first product thereon;
    rotating said first rotatably mounted internal body around a first axis that is inclined relative to a first horizontal plane;
    separating parts of said first product into a first plurality of processing sections defined by a second rotatably mounted internal body and a third rotatably mounted internal body within said first autoclave equipment, wherein said first rotatably mounted internal body, said second rotatably mounted internal body, and said third rotatably mounted internal body rotate around a first common rotating axis, wherein said first product enters into a first central rotating processing section defined in part by said first rotatably mounted internal body and is separated into parts migrating from said first central rotating processing section radially outwardly through holes in said first rotatably mounted internal body into one of said first plurality of processing sections, and wherein said second rotatably mounted internal body and said third rotatably mounted internal body are positioned radially further outwardly with respect to said first rotatably mounted internal body;
  performing a second autoclave process comprising:
    providing a second autoclave equipment, operating as either a continuous process or a batch process, said second autoclave equipment comprising a second outer pressure housing vessel and a fourth rotatably mounted internal body that supports a second product thereon;
    rotating said fourth rotatably mounted internal body around a second axis that is inclined relative to a second horizontal plane;
  wherein each of said first autoclave process and said second autoclave process being operated as a continuous process or a batch process, wherein each of said first autoclave process and said second autoclave process is operated with at least one variation of process settings for a respective one of said first autoclave equipment and said second autoclave equipment, said process settings being selected from the group consisting of
  pressure settings,
  temperature settings,
  moisture settings, and
  process dwell time settings.

6. The autoclave process according to claim 5, further comprising separating parts of said product by segregating parts of said product by size by passing larger parts through a first plurality of holes of said first rotatably mounted internal body of said first autoclave process and feeding said segregated parts of said product to said second autoclave process.

7. The autoclave process according to claim 6, wherein said first rotatably mounted internal body of said first autoclave process comprises holes of different size in different regions, through which differently sized parts of said product are passing and wherein said differently sized parts are fed to said second autoclave process.

8. An apparatus for sterilizing a product, comprising:
  an autoclave, wherein said autoclave comprises an outer pressure housing vessel and a rotating internal body that supports a product thereon, said rotating internal body is configured to rotate around a horizontally inclined axis and adapted to apply between 0 to 1 G of acceleration forces to said product;
  wherein said autoclave comprises a plurality of processing sections defined by a second rotating internal body and a third rotating internal body and adapted to allow said product or parts thereof to pass from one of said plurality of processing sections to a neighbouring one of said plurality of processing sections, and wherein said plurality of processing sections are essentially concentrically positioned around a common axis of rotation and further adapted to allow said product or parts thereof to pass from a central one of said plurality of processing sections that is defined by said rotating internal body towards another one of said plurality of processing sections that is radially outwardly positioned relative to said central one of said plurality of processing sections.

9. The apparatus according to claim 8, wherein said rotating internal body is adapted to rotate at a speed to cause avalanching of said product therein.

10. The apparatus according to claim 8, wherein said rotating internal body comprises an internal processing device selected from the group consisting of a product-shredding device, positioned so as to allow interaction with avalanching product or product parts, and further comprising multiple fingers without sharp edges so as to allow pulling apart rather than cutting of said product or parts thereof; and an opening device to allow opening up of pulp fibres, if present in said product.

11. The apparatus according to claim 8, wherein said rotating internal body comprises a first plurality of holes and said second internal rotating body comprises a second plurality of holes differing in size or shape to allow segregation and separation of parts of said product.

12. Autoclave equipment comprising:

a first apparatus for sterilizing a product comprising:

a first autoclave, wherein said first autoclave is adapted to operate in a continuous process mode or a batch process mode, and wherein said first autoclave comprises a first outer pressure housing vessel and a first rotating internal body that supports a first product thereon, said first rotating internal body is configured to rotate around a first horizontally inclined axis and adapted to apply between 0 to 1 G of acceleration forces to said first product, wherein said first autoclave comprises a first plurality of processing sections defined by a second rotating internal body and a third rotating internal body and adapted to allow said first product or parts thereof to pass from one of said first plurality of processing sections to a neighbouring one of said first plurality of processing sections, and wherein said first plurality of processing sections are essentially concentrically positioned around a first common axis of rotation and further adapted to allow said first product or parts thereof to pass from a central one of said first plurality of processing sections that is defined by said first rotating internal body towards another one of said first plurality of processing sections that is radially outwardly positioned relative to said central one of said first plurality of processing sections;

a second apparatus for sterilizing a product comprising:

a second autoclave, wherein said second autoclave is adapted to operate in a continuous process mode or a batch process mode, and wherein said second autoclave comprises a second outer pressure housing vessel and a fourth rotating internal body that supports a second product thereon, said fourth rotating internal body is configured to rotate around a second horizontally inclined axis and adapted to apply between 0 to 1 G of acceleration forces to said second product;

wherein said first autoclave and said second autoclave are adapted to operate with varying process settings, said process settings being selected from the group consisting of pressure settings,
temperature settings,
moisture settings, and
process dwell time settings.

13. The autoclave process according to claim 1, wherein said rotatably mounted internal body, said second rotatably mounted internal body, and said third rotatably mounted internal body rotate around a common rotating axis at different speeds or directions.

14. The autoclave process according to claim 6, wherein separating parts of said product by segregating parts of said product by size further comprises passing smaller parts through a second plurality of holes of said fourth rotatably mounted internal body of said second autoclave process.

15. The autoclave process according to claim 1, wherein said first product is a used hygiene/sanitary product.

16. The autoclave process according to claim 5, wherein said first product is a used hygiene/sanitary product.

* * * * *